(12) United States Patent
Leahy et al.

(10) Patent No.: US 7,030,166 B2
(45) Date of Patent: Apr. 18, 2006

(54) PROCESS TO ENHANCE CATALYST LIFE AND REMOVAL OF DEBRIS

(75) Inventors: James Leahy, Tulsa, OK (US); Juan Inga, Sapulpa, OK (US)

(73) Assignee: Syntroleum Corporation, Tulsa, OK (US)

(*) Notice: Subject to any disclaimer, the term of this patent is extended or adjusted under 35 U.S.C. 154(b) by 0 days.

(21) Appl. No.: 11/102,365

(22) Filed: Apr. 8, 2005

(65) Prior Publication Data

US 2005/0239911 A1 Oct. 27, 2005

Related U.S. Application Data

(60) Provisional application No. 60/560,572, filed on Apr. 8, 2004.

(51) Int. Cl.
C07C 27/00 (2006.01)

(52) U.S. Cl. ............ 518/709; 518/700; 518/705; 518/706

(58) Field of Classification Search ........... 518/700, 518/705, 706, 709

See application file for complete search history.

(56) References Cited

U.S. PATENT DOCUMENTS

| 5,260,239 A | * | 11/1993 | Hsia | ............ 502/30 |
| 5,498,638 A | | 3/1996 | Long | |
| 6,156,809 A | | 12/2000 | Clark et al. | |

* cited by examiner

*Primary Examiner*—J. Parsa
(74) *Attorney, Agent, or Firm*—Baker & McKenzie LLP; Valerie K. Friedrich

(57) ABSTRACT

A process to optimize a slurry Fischer-Tropsch catalyst life and to further optimize removal of debris from a slurry Fischer-Tropsch process is provided. The process passes a part of a Fischer-Tropsch Reactor slurry inventory to another upstream Fischer-Tropsch Reactor where the Fischer-Tropsch reactors are connected in series. The process utilizes either multiple or a single transfer vessel and optionally, a motive gas.

13 Claims, 2 Drawing Sheets

PROCESS TO ENHANCE CATALYST LIFE AND REMOVAL OF DEBRIS

CROSS REFERENCE TO RELATED APPLICATIONS

This application claims the benefit of U.S. Provisional Application No. 60/560,572, filed Apr. 8, 2004.

FEDERALLY SPONSORED RESEARCH

Not applicable.

REFERENCE TO MICROFICHE APPENDIX

Not applicable.

FIELD OF THE INVENTION

The invention relates to a process to improve catalyst life of a slurry Fischer-Tropsch ("FT") catalyst and to improve removal of debris arising from attrition of slurry FT catalyst particles. More specifically, the invention relates to a process wherein a regenerated slurry FT catalyst is fed in a countercurrent direction from the flow of syngas in a multiple Fischer-Tropsch reactor system wherein the reactors are connected in series.

BACKGROUND OF THE INVENTION

Fischer-Tropsch catalysts partially or wholly deactivate due to a variety of factors, including poisoning by nitrogen-containing or sulfur-containing compounds and physical degradation, or attrition, of the solid catalyst particles. The catalyst activity decline translates into a loss of hydrocarbon production. There are strong economic incentives to maintain catalyst activity and hydrocarbon production without introducing additional catalyst to the system. With decreasing activity, Fischer-Tropsch catalysts often also display increasing selectivity for lighter, i.e., $C_4$-, hydrocarbons.

Several methods of regenerating Fischer-Tropsch catalysts which have been deactivated are known. For example, a slurry Fischer-Tropsch catalyst may be regenerated by contacting the slurry with hydrogen or a hydrogen-containing gas. Yet other known processes contact the used catalyst with an oxygen containing gas or steam. Such processes may be used to remove carbon material from the catalyst surface or to alter the oxidation state of the active metal in the catalyst. In such processes, the catalyst must generally then be reactivated by a reduction step with a hydrogen-containing gas. In yet another known regeneration process, the spent catalyst is dissolved, the active metal is re-precipitated and recovered, and the catalyst re-manufactured using the recovered metal.

Catalyst activity is also lost by physical degradation. In all fluidized processes, catalyst particles suffer attrition to a certain extent. The degree of physical attrition is determined by the turbulence of the system and the strength of the catalyst particles. The degree of attrition may depend also on the process conditions in the Fischer-Tropsch reactor, such as the water partial pressure. The fines material product of attrition tends to accumulate in the Fischer-Tropsch Reactor (FTR) with a detrimental impact on the solid/liquid separation steps. The fines population is controlled by a fines removal process or frequent purging of the FTR, resulting in the loss of significant amounts of Fischer-Tropsch catalyst.

In virtually all known regeneration processes, the slurry taken from a specific Fischer-Tropsch reactor is returned to the same reactor after regeneration. Thus, the Fischer-Tropsch catalyst is subjected to the same conditions which led to deactivation.

There remains a need, therefore, for an improved and a more cost effective method to manage the Fischer-Tropsch catalyst and to increase the impact of catalyst regeneration.

SUMMARY OF THE INVENTION

A method to improve the Fischer-Tropsch catalyst performance in Fischer-Tropsch reactors in series by moving the slurry in a countercurrent circulation in which catalyst from downstream Fischer-Tropsch reactors is fed into one or more upstream Fischer-Tropsch reactors.

In some embodiments, part of or the whole catalyst inventory of a downstream Fischer-Tropsch reactor is sent to one or more upstream Fischer-Tropsch reactors. The slurry catalyst inventory is transferred by the use of a transfer vessel. In some embodiments of the invention, a motive gas is also used in transferring the slurry inventory in such countercurrent manner. In yet other embodiments of the invention, all or a part of the slurry inventory of a first stage Fischer-Tropsch reactor is passed to a regeneration unit. In some embodiments of the invention, the newly regenerated slurry is then fed into the last stage Fischer-Tropsch reactor.

DESCRIPTION OF EMBODIMENTS OF THE INVENTION

Slurry Fischer-Tropsch processes are known. In general, the slurry process involves introducing syngas into a hot reactive slurry in a reactor. The slurry includes Fischer-Tropsch product hydrocarbons and particulate Fischer-Tropsch catalyst. The Fischer-Tropsch product hydrocarbons are liquid at the reactor conditions so that the catalyst particles are dispersed therein, forming the slurry. The process of the invention may be used in connection with any Fischer-Tropsch slurry process.

Figure 1:
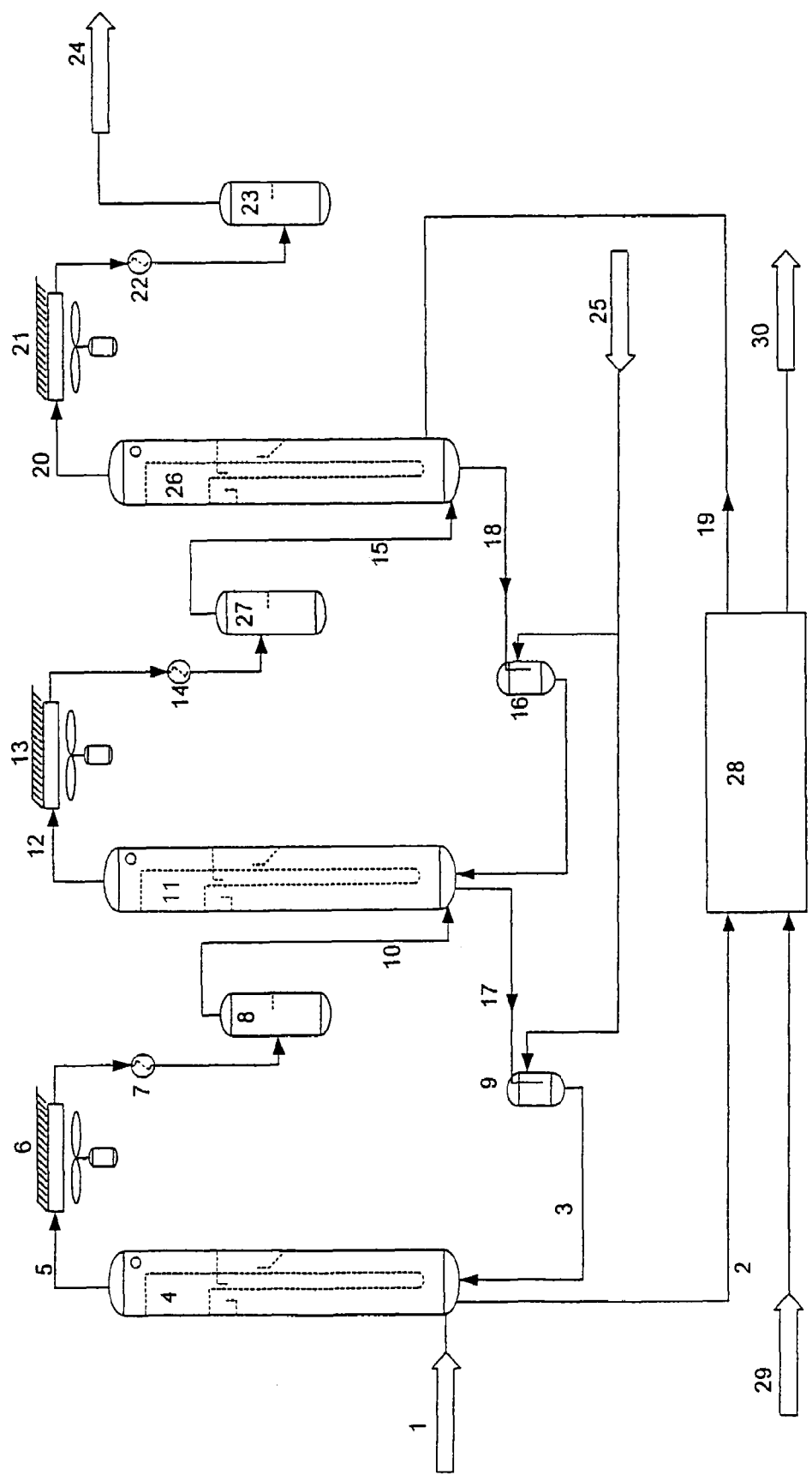
FIG. 1 is a schematic of a first embodiment of the process.

One embodiment of the process of the invention is shown in FIG. 1. Syngas 1 is introduced into a first stage Fischer-Tropsch reactor ("FTR") 4. The hydrocarbon products, unreacted syngas, water and other by-products may exit FTR 4 either as liquid or gaseous streams. As shown in FIG. 1, a first FTR effluent 5 is removed overhead. Effluent 5 which is composed primarily of $C_{4+}$ hydrocarbons with smaller amounts of $C_{4-}$ hydrocarbons, water and unreacted syngas is then cooled, preferably using an air-cooler 6 and optionally a water cooler 7. The cooled and condensed effluent 5 then enters a first separator drum 8. An overhead stream 10 consisting primarily of unreacted syngas is recovered from first separator drum 8 and fed into a second stage FTR 11. A second FTR effluent 12 may be recovered overhead from second stage FTR 11 and cooled, again preferably with an air-cooler 13 and optionally, a water cooler 14. The second cooled and condensed effluent 12 may be separated in a second separation drum 27. A second overhead stream 15 from second separation drum 27, which is also composed primarily of unreacted syngas may then be fed into a third stage FTR 26. Light hydrocarbon products exit third stage FTR 26 in a third FTR effluent 20 and may then be condensed, preferably, in air-coolers 21 and optionally, water coolers 22. The liquid products in the third FTR effluent 20 are then separated in a third separation drum 23. Tail gas 24, the overhead of the third separation drum 23, may be further processed for additional hydrocarbon production or may be used to generate power or stream.

Fresh catalyst 29 enters the process via a regeneration section 28. Fresh catalyst 29 is mixed with used catalyst slurry from first stage FTR 4 in regeneration section 28. Mixed slurry 19 is fed into the most downstream FTR, in this case to the third stage FTR 26. A portion of the slurry 18 from the third stage FTR 26 may be fed into transfer vessel 16. Motive gas 25 may be added to slurry 18 to increase the pressure of the slurry 18 in transfer vessel 16. Motive gas 25 may include, for example, nitrogen, natural gas, hydrogen or any stream having a higher pressure than the second stage FTR 11. Motive gas 25 should preferably not have a significant concentration of any component that may be detrimental to Fischer-Tropsch catalyst stability. A fraction of the slurry 17 from the second stage FTR 11 may be sent to a transfer vessel 9. Motive gas 25 is also used to raise the pressure of slurry 17 and to assist in transferring slurry 17 to the first stage FTR 4. In some embodiments, the transfer vessels used 9 and 16 may be the same vessel.

Figure 2:
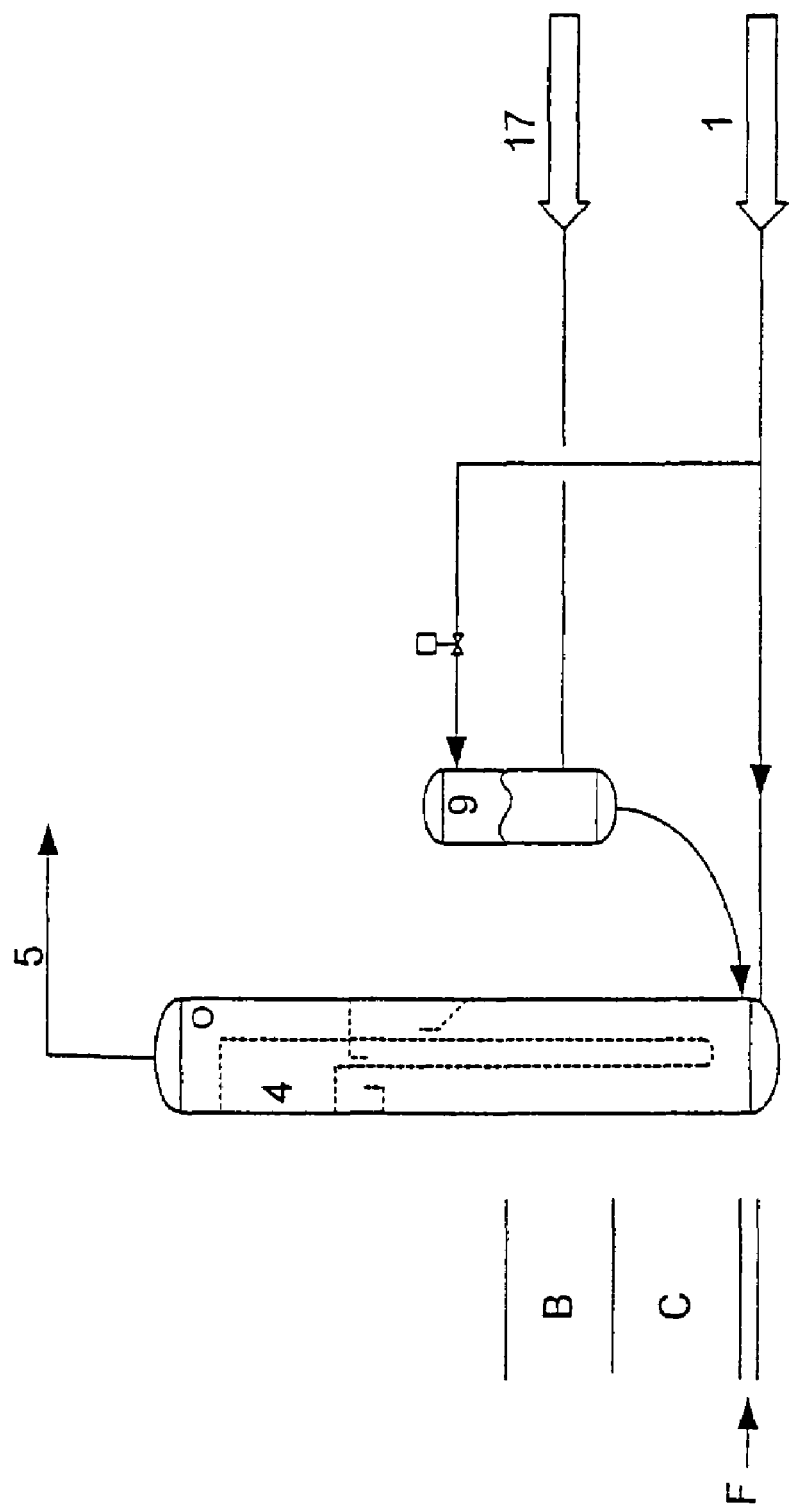
FIG. 2 is a schematic illustrating the pressure balance of the process.

FIG. 2 is a detail of the pressure balance permitting the countercurrent flow of slurry. Fischer-Tropsch slurry 17 from the second stage FTR 11 is passed into transfer vessel 9. Syngas 1 enters the bottom of first stage FTR 4 and is also used as a motive gas 25 to move the slurry 17 from transfer vessel 9 to FTR 4. The slurry stream 17 exits the bottom of transfer vessel 9 through a line 100 and is fed into the bottom of FTR 4.

The pressure at the end of line 100 can be described as the syngas pressure "F" plus the liquid head of B and C. On the other hand the pressure in the reactor at the same elevation can be described as the syngas pressure minus the gas expanded liquid head F. This means that the driving pressure of the slurry to enter the FTR will be the liquid head B plus the liquid head of C and the gas expanded liquid head F.

EXAMPLE 1

Hydraulics of FIG. 2

For example, the driving pressure is calculated for a process having the following characteristics: In an Fischer-Tropsch reactor having a diameter of 20 ft, with a Fischer-Tropsch slurry having a specific gravity of 1.3. The slurry inlet to the FTR is located 3 ft above the syngas inlet. The connecting pipe between the transfer vessel is 10 ft tall. The level of the slurry in the transfer vessel is 15 ft. The syngas pressure is 650 psig. The gas holdup in the FTR is 50% by volume.

The driving pressure at the beginning of the transfer is calculated as:

Pressure of the syngas+15 feet of slurry head+10 feet of slurry head minus the sum of (the syngas pressure and the 3 feet of expanded slurry head). The driving force in this numerical example is: 15 ft*1.3*62.37 lb/ft$^3$/144 inches$^2$/ft$^2$+10 ft*1.3*62.37 lbs/ft$^3$/144 inches+3 ft*1.3*62.37* (1−0.50)=14.92 lbs/ft$^2$.

EXAMPLE 2

Nitrogen Compounds Absorption

Two Fischer Tropsch reactors in series were operated with low nitrogen compound removals. The following table shows the amount of nitrogen-containing compounds in each of the first and second FTR feeds.

|  | Feed to 1st FTR (Online Sampling) | Feed to 2nd FTR (Bomb Sample) | Detection Limit |
| --- | --- | --- | --- |
| Flow | 240 lb/hr | 214 lb/hr |  |
| HCN | ~330 ppb | <20 ppb and dropping | >10 ppb |
| NH3 | <50 ppb | >120 ppb and increasing | >50 ppb |

EXAMPLE 3

Water Partial Profile

A simulation to calculate water partial pressures in each reactor of a three FTR in series was conducted. The results are shown in the Table below.

|  | Stage of Hydrocarbon Synthesis | | |
| --- | --- | --- | --- |
| Component | First | Second | Third |
| Water | 52.69 | 28.31 | 13.77 |

The process of the invention provides numerous features and advantages: For example, the regenerated catalyst is fed to a Fischer-Tropsch reactor that is protected from:
1. high partial pressure of water
2. high concentrations of nitrogen compounds
3. high carbon based deactivation since its productivity is the lowest Furthermore, deactivation due to nitrogen compound poisons is mostly confined to the first stage Fischer-Tropsch reactor. The catalyst fines, arising from attrition, are constantly purged from the system thereby reducing the required capacity of the solid/liquid separation devices in the whole plant.

What is claimed is:
1. A Fischer-Tropsch synthesis comprising the steps of:
   (a) feeding synthesis gas into a first slurry FTR and recovering a first effluent comprised of $C_{4+}$ hydrocarbons, water and unreacted syngas;
   (b) separating the unreacted syngas from the first effluent and feeding the unreacted syngas to a second slurry FTR;
   (c) withdrawing a second slurry portion from the second FTR slurry and transferring the portion to a first transfer vessel;
   (d) increasing the pressure of the second slurry portion in the first transfer vessel by feeding a motive gas to the transfer vessel wherein the motive gas has a pressure greater than the second FTR;
   (e) feeding the second slurry portion from the first transfer vessel into the first FTR; and
   (f) withdrawing a first slurry portion from the first FTR.
2. The process of claim 1 further comprising the step of (h) adding new catalyst to the regenerated slurry.
3. The process of claim 1 wherein the regeneration section comprises a process to reactivate chemically deactivated FT catalyst.
4. The process of claim 2 wherein the regeneration section comprises mixing new catalyst with the first slurry portion.

5. The process of claim 1 wherein the motive gas has a pressure of 5 psi or greater than that of the first FTR.

6. The process of claim 1 wherein the motive gas is injected at a bottom portion of the transfer vessel.

7. The process of claim 1 wherein the motive gas is selected from the group of syngas, high pressure process hydrogen, natural gas, and high-pressure process nitrogen.

8. The process of claim 1 further comprising the steps of:
(g) feeding the regenerated slurry to the second FTR.

9. The process of claim 1 further comprising the steps of:
(i) recovering from second FTR a second effluent from second FTR comprising $C_{4+}$ hydrocarbons, water and unreacted syngas; and
(ii) separating the unreacted syngas from the second effluent and feeding it to a third slurry FTR.

10. The process of claim 9 further comprising the steps of:
(iii) feeding the regenerated slurry to the third FTR.

11. The process of claim 10 further comprising the steps of:
(I) withdrawing a third slurry portion from the third FTR and transferring the third slurry portion to a second transfer vessel;
(II) third slurry portion to the second FTR.

12. The process of claim 11 wherein the first and second transfer vessels are the same vessel.

13. The process of claim 1 wherein the first slurry portion from the first FTR is transferred to a regeneration section to produce a regenerated slurry.

* * * * *